(12) United States Patent
Emmert et al.

(10) Patent No.: US 8,336,371 B2
(45) Date of Patent: Dec. 25, 2012

(54) REAL-TIME, ON-LINE ANALYSIS FOR THE QUANTIFICATION OF TRIHALOMETHANE SPECIES WITHIN DRINKING WATER SUPPLIES

(75) Inventors: Gary Lynn Emmert, Collierville, TN (US); Michael Andrew Brown, Memphis, TN (US)

(73) Assignee: University of Memphis Research Foundation, Memphis, TN (US)

( * ) Notice: Subject to any disclaimer, the term of this patent is extended or adjusted under 35 U.S.C. 154(b) by 436 days.

(21) Appl. No.: 12/116,943

(22) Filed: May 7, 2008

(65) Prior Publication Data

US 2009/0277255 A1 Nov. 12, 2009

(51) Int. Cl.
*G01N 30/84* (2006.01)
(52) U.S. Cl. ...................... 73/61.55; 73/61.52
(58) Field of Classification Search .............. 73/61.41, 73/61.43, 61.44, 61.52, 61.53, 61.55, 61.56, 73/61.58, 61.59
See application file for complete search history.

(56) References Cited

U.S. PATENT DOCUMENTS

| | | | |
|---|---|---|---|
| 5,358,557 A | 10/1994 | Jiang et al. | |
| 5,435,169 A | 7/1995 | Mitra | |
| 5,492,838 A * | 2/1996 | Pawliszyn | 436/178 |
| 5,762,808 A | 6/1998 | Peyton | |
| 5,814,128 A | 9/1998 | Jiang et al. | |
| 5,911,882 A | 6/1999 | Benjamin et al. | |
| 6,106,725 A | 8/2000 | Hong | |
| 6,368,559 B1 | 4/2002 | Galletti et al. | |
| 6,408,227 B1 | 6/2002 | Singhvi et al. | |
| 7,186,344 B2 | 3/2007 | Hughes | |

FOREIGN PATENT DOCUMENTS

JP 4-74582 * 3/1992 ................ 203/11

OTHER PUBLICATIONS

Emmert, G.L. et al., "Measuring Trihalomethane Concentrations in Water Using Supported Capillary Membrane Sampling-Gas Chromatography", Talanta, vol. 63, 2004, pp. 675-682.*
Brown M.A. et al., "On-Line Monitoring of Trihalomethane Concentrations in Drinking Water Distribution Systems Using Capillary Membrane Sampling-gas Chromatography", Analytica Chimica Acta, vol. 555, 2006, pp. 75-83.*
Gems, G. et al., Measuring the concentrations of drinking water disinfection by-products using capillary membrane sampling-flow injection analysis, Water Research 39 (2005) 3827-3836.
Simone Jr., P.S., et al., On-line monitoring of µg/L levels of haloacetic acids using ion chromatography with post-column nicotinamide reaction and fluorescence detection, Analytica Chemica Acta 570 (2006) 259-266.

* cited by examiner

*Primary Examiner* — Daniel Larkin
(74) *Attorney, Agent, or Firm* — Wyatt, Tarrant & Combs, LLP; William S. Parks

(57) ABSTRACT

Separating trihalomethanes from drinking water samples (via a process such as capillary membrane sampling, and the like) followed by gas chromatograph analysis to determine quantity measurements and species identification of such trihalomethane (THM4) contaminants therein is provided. With the necessity to chlorinate drinking water to remove harmful bacteria and other potential toxins, trihalomethane byproducts are generated that may harm humans after consumption as well due to suspect carcinogenicity of such compounds. A reliable manner of measuring such drinking water supplies for such THM4 contaminants at locations far from the source and closer to dispensers is highly desirable. The ability to separate the THM4 from the drinking water sample, followed by a gas chromatography or like manner of quantifying and identifying the THM4 compounds possibly present within the drinking water sample has been found to be nearly as reliable as federally mandated source measuring methods for the same purpose, but with the versatility to measure for such trihalomethane contaminants anywhere along the drinking water supply line.

2 Claims, 4 Drawing Sheets

REAL-TIME, ON-LINE ANALYSIS FOR THE QUANTIFICATION OF TRIHALOMETHANE SPECIES WITHIN DRINKING WATER SUPPLIES

FIELD OF THE INVENTION

The present invention relates to separating trihalomethanes from drinking water samples (via a process such as capillary membrane sampling, and the like) followed by gas chromatograph analysis (CMS-GC) to determine quantity measurements and species identification of such trihalomethane (THM4) contaminants therein. With the necessity to chlorinate drinking water to remove harmful bacteria and other potential toxins, trihalomethane byproducts are generated that may harm humans after consumption as well due suspected carcinogenicity of such compounds. A reliable manner of measuring such drinking water supplies for such THM4 contaminants at locations far from the source and closer to dispensers is highly desirable. The ability to separate the THM4 from the drinking water sample, followed by a gas chromatography or like manner of quantifying and identifying the THM4 compounds possibly present within the drinking water sample has been found to be nearly as reliable as federally mandated source measuring methods for the same purpose, but with the versatility to measure for such trihalomethane contaminants anywhere along the drinking water supply line.

BACKGROUND OF THE INVENTION

Drinking water has been, and continues to be, heavily treated for bacteria and other microscopic organisms that may cause infection in humans and other animals subsequent to consumption. In order to disinfect water supplies, halogenated materials have been introduced therein that have proven more than adequate for such a purpose. Unfortunately, although such halogenated compounds (chlorinated and chloraminated types, primarily) exhibit excellent disinfection capabilities, when present within aqueous environments at certain pH levels these halogenated compounds may generate byproducts that may themselves create health concerns. The United States Environmental Protection Agency (USEPA) in fact regulates four types of trihalomethanes (THM4) within drinking water. These THM4 are chloroform, bromoform, dibromochloromethane, and bromodichloromethane. Removal of such compounds from drinking water is not possible as for typical chlorinated and brominated disinfecting compounds, at least not at the same reliability level as for the disinfecting agents. Thus, residual amounts may remain within treated water supplies that may require further removal processing to be undertaken, or avoidance of ingestion if necessary. Of course, if the level of contamination is sufficiently low, initiation of such potentially expensive removal steps would be unwise from an economic perspective.

The USEPA currently has set a maximum contaminant level for these THM4 in drinking water of 0.080 mg/L. It is thus important to reliably analyze and measure the total amount of such contaminants in order to determine if removal if necessary.

The USEPA has instituted its own testing methods for such a purpose. For THM4, the primary test method is 502.2. The USEPA 502.2 method measures for individual and total THM4 as well as other volatile byproducts. This method utilizes a TRACOR® 540 gas chromatography with Hall/PID detectors, a Tracor LSC-2 sample concentrator, and a TEK-MAR® 2050 Autosampler. Such a system is, again, very effective at measuring drinking water samples at the source, but remote analyses are not readily available as the entire system is too cumbersome to move to locations along a drinking water line. As such, on-line analysis through these protocols is difficult, expensive, and labor intensive to implement.

Measurement at the source (i.e., within a water purification plant location) may be effective for system-wide average readings; however, in the large supplies of water at such locations, the chances of proper sampling to that effect may be suspect since the contaminants may be present in varied locations, rather than definitely mixed throughout the tested water supply itself. Additionally, testing may not uncover the actual level of residual THM4 disinfection byproducts prior to the water supply being disbursed to distant dispense sites (transfer pipes, homes, schools, businesses, etc.). In any event, there is a relatively new rule in place that requires utilities to provide evidence of compliance with trihalomethane levels at multiple locations, rather than a straightforward system-wide average. There is thus a drive to implement remote testing via real-time, on-line methods for water supply THM4 contaminant level measurements.

Such a desirable on-line procedure has been difficult to achieve, however, particularly as it pertains to the determination of not only the total amount of THM4 within water supplies, but also the amount of each species of the same THM4 groups present within the tested water source. High performance liquid chromatography, utilizing electrospray ionization-mass spectrometry or ultraviolet absorbance detector, has been attempted. The sensitivity and selectivity of the high performance liquid chromatography methods are easily sacrificed without the cumbersome preparations in place, therefore requiring operator intervention during analysis. Again, this issue leads to serious drawbacks when on-line implementation is attempted.

Another methodology that has proven effective to a degree is post-column reaction-ion chromatography. This has shown promise, but only in terms of quantifying bromate ion concentrations in drinking water samples at a single microgram per liter level. This dual selectivity form (separation by ion chromatography column as well as the selective reaction with the post-column reagent with the analyte) offers an advantageous test method over the others noted above, except for the presence of more common anions, specifically chloride, at much higher concentrations within the sampled drinking water supply (mg/L instead of microgram). Separation of the THM4 species from other halogenated compounds (such as haloacetic acids), however has been problematic and caused certain degrees of interference in measuring total levels of both types of compounds within drinking water samples. Despite this problematic limitation, it was determined that fluorescence detection provided a much-improved detection protocol in comparison with ultraviolet and mass spectrometry possibilities, particularly for haloacetic acid concentrations. Thus, although such a fluorescence method of detection, coupled with the post-column reaction (again with nicotinamide reactant) and ion chromatography, exhibited the best results in terms of an on-line test method for haloacetic acid drinking water contaminant measurement levels, there remained a definite need for improvements in individual and total trihalomethane measurements and identifications within such test samples. To date, however, there has not been an analytical test protocol that has permitted implementation of such a system within an on-line real-time monitoring procedure with an acceptable degree of reliability. An automated system that provides such versatility and reliability has simply not been forthcoming within the pertinent art.

ADVANTAGES AND SUMMARY OF THE INVENTION

Accordingly, it is an advantage of the present invention to provide a reliable on-line drinking water analytical protocol for determining both the identity and individual measurements for the four different trihalomethanes that are commonly present as disinfection byproducts within such water sources. It is an additional advantage of the invention to provide reliability similar to that exhibited by 502.2 USEPA test method series described above, but at any location along a drinking water supply line and without need for operator involvement.

Accordingly, the instant invention encompasses a method of analyzing drinking water samples comprising the steps of:

a) providing at least one stream of drinking water that has been disinfected with chlorinated or chloraminated materials;

b) delivering said at least one stream of drinking water through a device that effectively separates volatile trihalomethane compounds that may be present within said at least one stream from said at least one stream; and c) delivering the separated trihalomethane sample through a multi-port valve for selective delivery to a chromatography analyzer, wherein said analyzer quantifies the amount of trihalomethanes present within said trihalomethane samples, which provides a reliable measurement of total amounts of such trihalomethanes within said at least one stream of drinking water, wherein said multi-port valve alternates between delivering said separated trihalomethane sample and a purging gas stream through to said chromatography analyzer by way of an actuator. Also encompassed within this invention is a drinking water analytical instrument comprising a capillary membrane sampling device for a drinking water stream trihalomethane separation process, wherein said device is attached to a multi-port valve which selectively delivers either the separated trihalomethane stream or a purging gas stream to a chromatography analyzer.

Such a procedure and analytical instrument may be set up remotely and without human operator involvement, at any location along a drinking water supply line. The multi-port (preferably either 8- or 10-port) valve permits alternating streams either drinking water contaminants to be measured (specifically separated THM4 compounds) or just GC carrier gas.

The separation of trihalomethanes from the drinking water stream(s) may be performed by a capillary membrane sampling device. In this manner, the drinking water stream is introduced within the device and the volatile trihalomethane compounds permeate across thin silicone membrane tubing and out of the drinking water stream itself for separation therefrom into a carrier gas stream (again, nitrogen, is preferred, though not necessary; other inert gases may be used alone or in combination if desired). In this manner, it is possible for the trihalomethanes to be separated from other contaminants within the drinking water stream that may compromise quantifications of such compounds subsequently due to reactions between such THM4 compounds and such other potential contaminants, among other reasons. A carrier gas (such as nitrogen) may be employed within the capillary membrane device to promote diffusion of the volatile THM4 compounds from the drinking water stream within the device itself.

The chromatography analyzer may be any type that permits quantification of such THM4 species. Most preferable are gas chromatographs (GCs) equipped with electron capture detectors (such as a Ni-63 type). Such instruments exhibit excellent separation and quantification of volatile THM4 compounds.

As noted above, such a method permits quantification of individual and total trihalomethane species within the subject drinking water sample to determine the potential harmful levels of such suspect carcinogenic compounds therein. The method and the entire instrument may be operated remotely without human operator involvement, at any location along a drinking water supply line.

Such methods have permitted implementation of remote automatic testing procedures and instrumentation along any location of a drinking water supply line. As noted above, the previous analytical approaches suffered from necessary operator involvement, deleterious effects from reactants or simultaneously formed byproducts thwarting reliable measurements from being taken to ensure compliance with federal regulations. This present method and entire analytical instrument has overcome such limitations through the inclusion of a multi-port valve to permit delivery of the separated trihalomethane compound stream to the chromatography analyzer. In this manner, the reliability of such a GC step is available through a remote detection process. The instrumentation does not require human operator involvement unless a breakdown or energy source failure occurs; for testing purpose, however, the analyses can be performed at regular intervals through computer processor control.

DETAILED DESCRIPTION OF THE DRAWINGS AND PREFERRED EMBODIMENTS OF THE INVENTION

Figure 1:
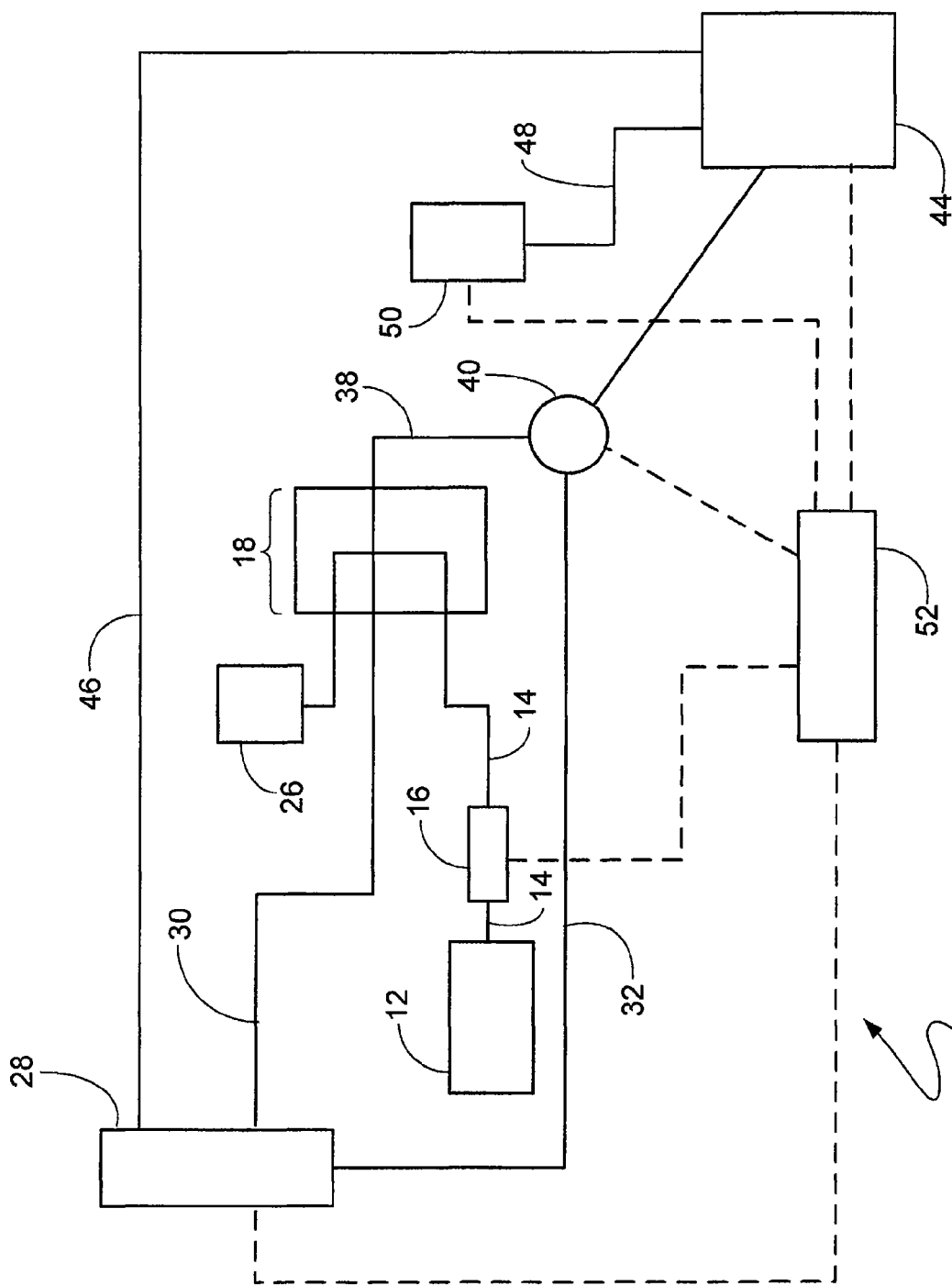
FIG. 1 depicts a broad schematic of the THM4 separation-GC analyzer utilized for the on-line inventive total THM4 measurement and identification procedure.

As shown in FIG. 1, the overall system basically includes an gas chromatogram-electron capture detection analyzer 44 (Buck Scientific-model 610) with a capillary membrane sampling device 18 that initially separates the volatile trihalomethanes from a drinking water sample stream 14 into a separate gas carrier stream 30 (such as nitrogen, as one example). The initial drinking water sample stream 14 is supplied through from a tap source 12 via a pump 16 (such as, without limitation, a peristaltic pump Cole-Parmer). The water stream 14 is delivered to a separating device 18 simultaneously with the carrier gas stream 30 (supplied by a gas source, such as nitrogen 28, that also supplies the GC-ECD 44 via a feed line 46, and the carrier gas stream 32 that leads directly to the valve 40; this multiple source is for efficiency; any number of gas sources may be utilized for these purposes, however), at which point the volatile THM4 compounds are subject to diffusion through a membrane from the water stream 14 to the gas stream 30. The water stream 14 then empties into a waste receptacle 26, and the gas stream now containing THM4 compounds 38 is delivered to a multi-port valve 40 (more fully described in FIGS. 3 and 4, below). Simultaneously, a second carrier gas stream 32 runs directly to the same multi-port valve 40 though enters therein at a different port than the THM4 gas stream 38. This valve 40 is fully automated using a software package (such as Peak Simple from SRI Instruments Inc., as one example). The valve 40 permits alternating injection of either the GC carrier gas stream 32 or the THM4 gas stream 38 into a GC-ECD instrument 44. In this manner, the GC carrier gas stream 32 supplies GC-ECD 44 regularly for reliable measurements of THM4 compounds to be made at selected time intervals. A helium gas source 50 is utilized to feed into the GC-ECD 44 via a feed line 48 as well. A computer processor 52 is utilized to control the pump(s) 16, gas sources 28, 50, valve 40, and GC-ECD 44 to permit remote measurements within operator involvement.

Figure 2:
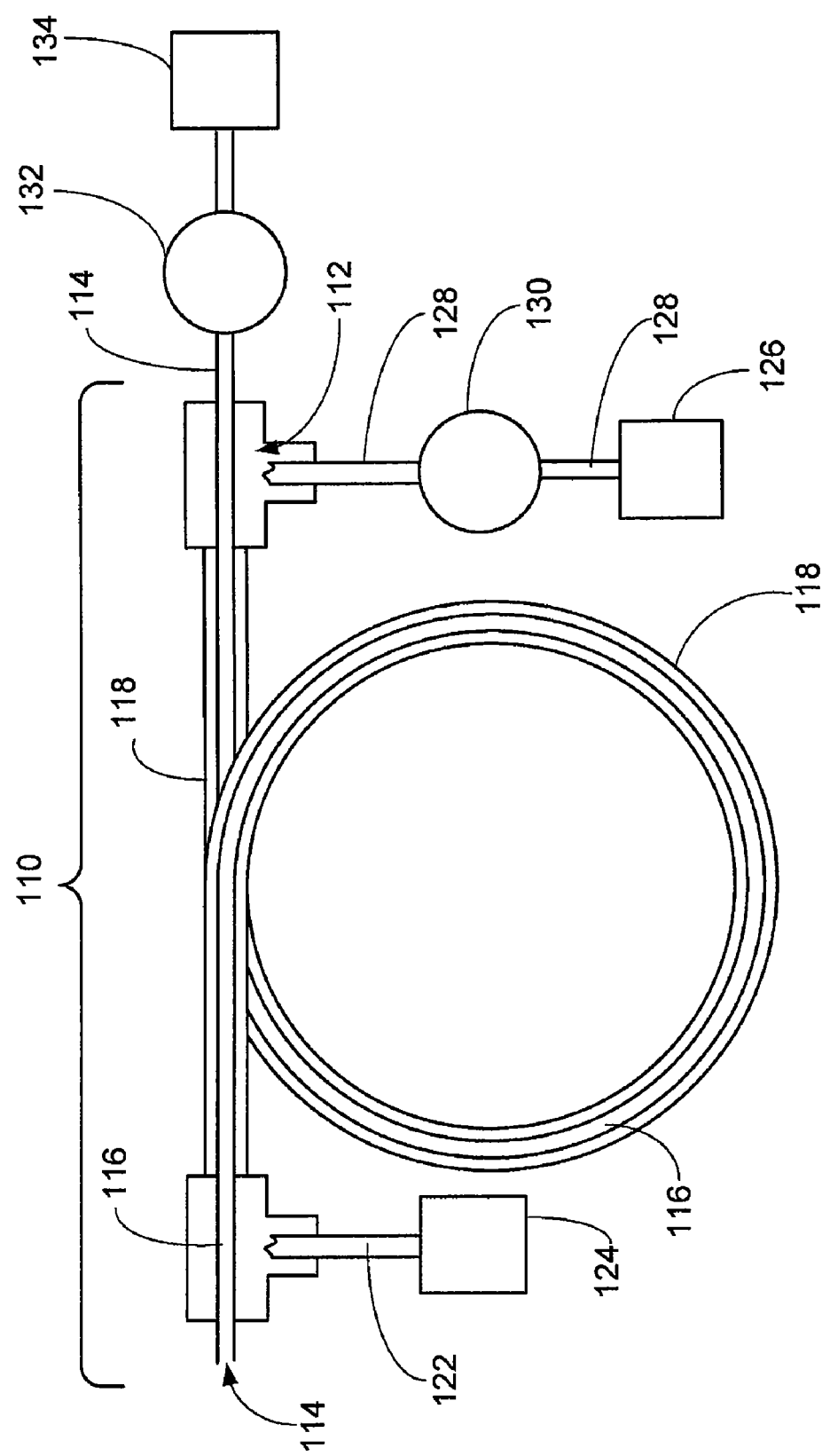
FIG. 2 depicts a closer view of the capillary membrane sampling devices attached to a multi-port valve within the device of FIG. 1.

In FIG. 2, the capillary membrane sampling component 110 is shown wherein the individual trihalomethanes are extracted from the drinking water sample stream 112. This stream 112 flows within the CMS 110 in a direction opposite that of the nitrogen carrier gas stream 114 that flows through an inner feed line 116 (being a smaller silicone membrane tubing such as from Dow Corning, for example) that samples from inside the larger water stream feed line 118 that is made from an inert material (such as TEFZEL®, from Valco Instruments) or from a batch sample. The inner feed line 116 is permeable to the volatile trihalomethanes such that diffusion through the membrane occurs for such contaminants. As such, upon introduction of the drinking water sample stream 112 therein permits extraction of these THM4 compounds therefrom readily and nearly completely (if not completely). The carrier gas stream 114 thus takes the total THM4 compounds and is delivered through the CMS 110 through the inner feed line 116 to a multi-port valve 132 for further delivery, selectively, to a GC-ECD instrument 134. In one potentially preferred embodiment, a water tap 126 is fed into the CMS 110 via a water feed line 128 through a pressure regulator/restrictor 130 and into the water stream feed line 118 within the CMS 110 to deliver the water stream thereto. As it passes through the CMS, again in a direction opposite that of the carrier gas stream 114, the water stream 118 is extracted of (to a large degree, at least) THM4 compounds then passes through an exit line 122 into a waste receptacle 124.

Figure 3:
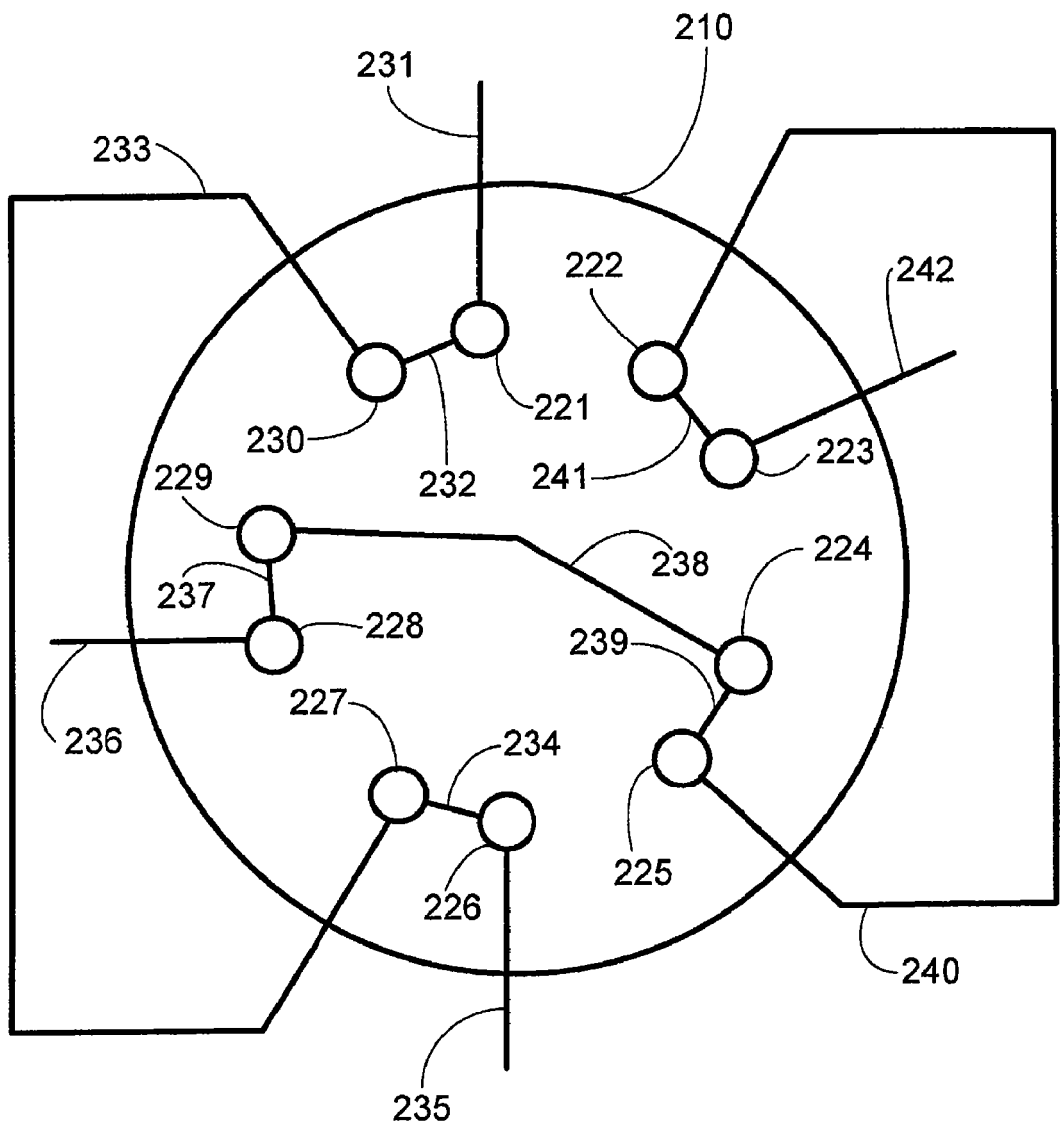
FIG. 3 depicts a preferred ten-port valve of FIG. 1 in closer view.

In FIG. 3, the ten-port valve 210 (broadly 40 of FIG. 1) is shown in greater detail and in relation to delivering the THM4-containing carrier gas stream (114 of FIG. 2) into the GC-ECD (44 of FIG. 1). This valve 210 includes, as the name suggests, 10 individual ports 221, 222, 223, 224, 225, 226, 227, 228, 229, and 230. These ports 221 through 230 are configured to alternate target delivery ports by utilization of a non-illustrated disk. Such a disk will either allow transport from one port to another or cut off the supply and allow for movement from and/or to another port instead. Thus, in FIGS. 3 and 4, the first port 221 always delivers THM4 gas stream via a first line 231 into the valve 210 and the sixth port 226 always delivers the THM4 gas stream into a waste receptacle (not illustrated) via an exit line 235. The THM4 gas stream will do so in a first position (that depicted in FIG. 3), whereby the gas stream is delivered through the first port 221 to the tenth port 230 through a second line 232, then from the tenth port 230 to the seventh port 227 through a first loop line 233, then to the sixth port 226 via a fourth line 234. Simultaneously, in this position, the GC carrier gas stream enters the valve 210 through a carrier gas injection line 236 into the eighth port 228 then to the ninth port 229 via a seventh line 237, then through a middle line 238 to the fourth port 224, to the fifth port 225 via a ninth line 239, then to the second port 222 through a second loop line 240, then to the third port 223 via an eleventh line 241, and out to the GC-ECD line 242.

Figure 4:
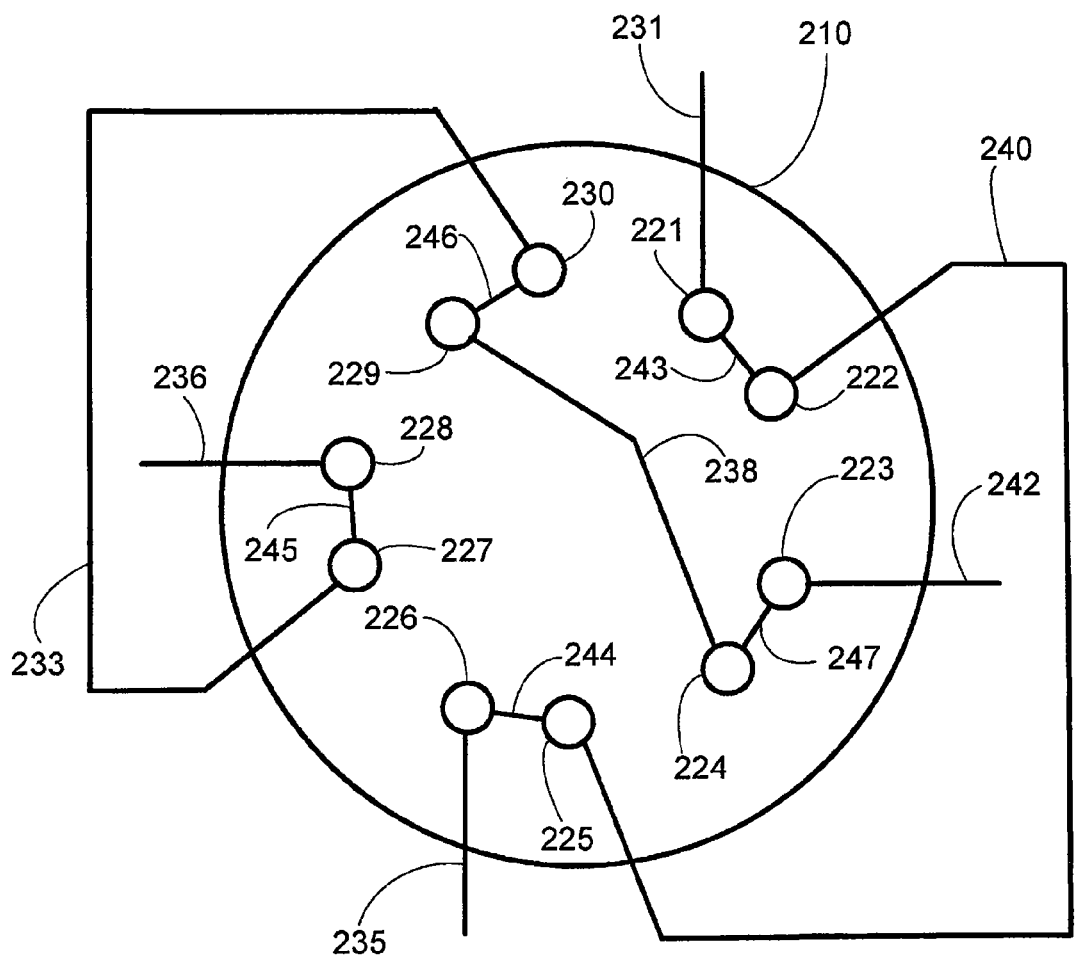
FIG. 4 depicts a different alternate position of the ten-port valve of FIG. 3.

During this specific configuration of the valve 210, the trihalomethane-containing gas stream is continuously flowing through the first loop line 233 until the valve 210 alternates to the position of FIG. 4, while the carrier gas stream is delivered to the GC-ECD (44 of FIG. 1) for purging of the instrument and other lines. Upon reconfiguring of the arrangement through the aforementioned non-illustrated actuator, the delivery of the THM4 gas stream is basically reversed. At that time, the FIG. 4 arrangement is in place. All the trihalomethane-containing gas stream that was remaining in the first loop line 233 at the moment the actuator reconfigured the valve 210 is then carried by the carrier gas stream to the GC-ECD (44 of FIG. 1) and on for the separation of the THM4 species and analyses. At that instant, the THM4 gas stream is then diverted to transport through the second loop line 240 via different lines 243, 244 and through the second, fifth, and sixth ports 222, 225, 226 to the same waste receptacle (not illustrated) through the same exit line 235. Likewise, the GC carrier gas stream (now including the residual THM4 gas stream that had been located within the first loop line 233 at the moment of reconfiguration) is rerouted but still ends up transporting to the GC-ECD (44 of FIG. 1) through different lines 245, 246, 247 and through the eighth, seventh, tenth, ninth, fourth, and third ports 228, 227, 230, 229, 224, 223 (in that order) until exiting the valve 210 through the GC-ECD feed line 242. The valve 210 may be made of any type of material, as may the ports 221-230, and the lines 231-247, although polymeric materials (such as polystyrene and polycarbonate, preferably) may be utilized for such a purpose. The lines 231-247 may actually be of any length, with about 30 cm preferable, particularly with the loop lines 233, 240.

In this manner, the THM4 compounds are separated from the drinking water sample via CMS, and then delivered to the GC-ECD for analysis, and the GC-ECD (as well as the entire carrier gas stream line) may be purged regularly. Such a system can be implemented at any location and, through automation, does not require continued operator input or control. The peristaltic (Cole-Parmer, or other types equivalent to said) pumps are controlled through computer software or other type of automation, thereby allowing, again, for remote utilization. Additionally, the entire system may be set up for wireless communication from a remote location to a central location for review of the analytical results. The main issue in terms of proper selectivity of such a system for such a purpose is the reliability thereof at such remote locations. In order to determine the feasibility of such an analytical method, it was first necessary to compare the results thereof to standard USEPA methods.

The preceding examples are set forth to illustrate the principles of the invention, and specific embodiments of operation of the invention. The examples are not intended to limit the scope of the method. Additional embodiments and advantages within the scope of the claimed invention will be apparent to one of ordinary skill in the art.

Two specific methods have been followed by water utilities for compliance measurements, albeit from the water source itself. In terms of such source measurements, however, these standards (USEPA 502.2 and 524.2 test protocols) have been the most reliable. Comparisons of drinking water samples for similar measurements through these compliance standard tests and those of the instant inventive method were undertaken. If the measurements were actually similar in amounts, identifications, and standard deviations, it would be properly assumed that the new method would be significantly reliable to the degree required under Federal regulations.

The USEPA 502.2 method measures for individual and total THM4 as well as other volatile byproducts. This method utilizes a TRACOR® 540 gas chromatography with Hall/PID detectors, a Tracor LSC-2 sample concentrator, and a TEKMAR® 2050 Autosampler. The sample preparations, collections and analyses were performed pursuant to those described within this specific methodology, except that the GC oven was increased in temperature in order to shorten the analysis time necessary for proper THM4 identifications and measurements. The MDLs for the THM4 compounds were 0.4 μg/L each for bromoform and chloroform, 0.6 μg/L each for bromodichloromethane and dibromochloromethane; the mean percent recoveries for these species were 96.7%, 101%, 98.6%, and 98.6%, respectively. The relative standard deviations for this method were 4.9%, 4.6%, 6.5%, and 6.4%, respectively, as well.

Thus, as noted above, it was important that the system devised exhibit similar results for these measurements. However, optimization of the separation capabilities and collection of only the compounds for which measurement and identification were necessary was required initially. Several optimization studies that varied flow rates, temperatures, were performed. Optimizations studies focused on the capillary membrane device and the chromatography analyzer mentioned above to provide sufficient quantifying of THM4. It was important to provide a capillary membrane sampling device that would selectively exclude any such species. Therefore premonitoring surveys were conducted as well to identify any interfering species real samples. The permeation of such species was prevented, or at least reduced to the level that any such species that did permeate the subject membrane would not interfere with the THM4 measurements.

Thus, after such optimization was put in place, drinking samples were then tested in accordance with the device described supra. Initial standard samples of THM4 were injected therein (20.0 μg/L THM4) followed by several deionized (reagent) water samples to clean out the system (this reagent water blank sample was tested for 1 hour, every 15 minutes therein, to determine if any residual effect problems would exist after such intervals of time had passed between tests. It was found that after one hour the amount of residual THM4 remaining within the overall system was de minimis and would not affect any further testing results. Thus, at least from this standpoint, uniform hourly, interval analyses would be possible.

Initial standards of different concentrations were then prepared of the THM4 compounds in order to generate calibration curves thereof. As is customary, the peak area of the chromatogram of individual THM4 was plotted as a function of concentration (μg/L). In terms of these initial calibration studies, the MDLs of each compound were very promising in comparison with those of the USEPA Test Methods 502.2, undertaken and described above MDL for chloroform was 0.3 μg/L, the mean recovery was 100%, and the relative standard deviation value was 4.5%; for bromodichloromethane the MDL was 0.5 μg/L, the mean recovery was 104%, and the relative standard deviation value was 8.6%; for dibromochloromethane the MDL was 0.3 μg/L, the mean recovery was 125%, and the relative standard deviation value was 3.5%; and for bromoform the MDL was 0.3 μg/L, the mean recovery was 124%, and the relative standard deviation value was 4.3%. The calibration curves thus provided an acceptable measuring stick with which to calculate the concentrations of the actual unknown drinking water sample values for the THM4.

Within both chlorinated and chloraminated treated water systems, samples were drawn and tested within the inventive system (CMS-GC) and the 502.2 test method. For the chlorinated water samples, the testing was performed over a 131 hour period; for the chloraminated, a 71 hour time period. Concentrations of THM4 were monitored at a rate of 1 sample per hour (with every $12^{th}$ hour excluded in order to run a standard control) through the inventive analyzer; for each USEPA method, for the first two days of sampling, measurements were taken every hour, followed by one sample every two hours thereafter. There were 72 comparison values for USEPA 502.2 to CMS-GC.

The concentration of chloroform range from 0.1 to 0.4 μg/L for USEPA 502.2 and from 0.1 to 0.4 μg/L for CMS-GC. The average concentration measured by USEPA 502.2 was 0.2±0.1 μg/L and using CMS-GC was 0.1±0.0 μg/L. The bias between the CMS-GC method and USEPA 502.2 ranged from −0.2 to 0.3 μg/L with an average of −0.1±0.1 μg/L.

The bromodichloromethane concentration ranges from 0.2 to 0.8 μg/L for USEPA 502.2 and 0.2 to 0.5 μg/L for CMS-GC. The average concentration was 0.5±0.2 μg/L for USEPA 502.2 and 0.3±0.1 μg/L for CMS-GC. The bias ranged from −0.5 to 0.2 μg/L (averaging −0.1±0.2 μg/L) for CMS-GC.

For dibromochloromethane, the concentrations ranged from 0.2 to 1.5 μg/L for USEPA 502.2, 0.3 to 0.9 μg/L for CMS-GC. The average concentration was 0.8±0.2 μg/L for USEPA 502.2 and 0.6±0.1 μg/L for CMS-GC. Using CMS-GC, the bias ranged from −0.9 to 0.4 μg/L with an average bias of −0.2±0.2 μg/L.

The concentration of bromoform ranged from 0.1 to 2.1 μg/L using USEPA 502.2 and 0.1 to 1.2 μg/L using CMS-GC. The average concentration was 0.5±0.3 μg/L using USEPA 502.2 and 0.4±0.2 μg/L using CMS-GC. Using CMS-GC, the bias ranged from −0.9 to 0.7 μg/L with an average of −0.2±0.3 μg/L.

The concentrations of each individual THM4 species were summed to obtain total THM4. The total THM4 concentrations ranged from 0.7 to 4.1 μg/L using USEPA 502.2 and 0.7 to 2.2 μg/L using CMS-GC. The average concentration was 1.9±0.7 μg/L using USEPA 502.2 and 1.4±0.3 μg/L using CMS-GC. Using the CMS-GC, the bias ranged from −2.4 to 0.9 μg/L with an average of −0.5±0.6 μg/L. The two methods both USEPA 502.2 and the inventive method agreed well.

For the chloraminated water supply there were 51 comparison values for USEPA 502.2 and CMS-GC. The concentration for chloroform ranged from 35.8 to 51.9 μg/L for the USEPA Method, from 31.3 to 44.5 μg/L for CMS-GC. The average concentration for USEPA 502.2 is 42.5±3.4 μg/L and for CMS-GC is 40.4±3.0 μg/L. Using CMS-GC, the bias ranged from −13.9 to 6.8 μg/L with an average of −1.5±4.9 μg/L, The concentration of bromodichloromethane ranged from 7.1 to 12.7 μg/L using USEPA 502.2 and 9.7 to 14.7 μg/L using CMS-GC. The average concentration was 9.2±1.0 μg/L for USEPA 502.2 and 12.8±1.5 μg/L for CMS-GC. The bias ranged from 0.0 to 7.2 μg/L with average of 3.7±1.6 μg/L The dibromochloromethane concentrations ranged from 1.1 to 2.1 μg/L using USEPA 502.2 and 1.4 to 2.5 μg/L using CMS-GC. The average concentration was 1.5±0.2 μg/L using USEPA 502.2 and 2.0±0.3 μg/L using CMS-GC. Using CMS-GC, the bias ranged from −0.3 to 1.2 μg/L, with an average of 0.4±0.3 μg/L.

None of the methods detected bromoform in chloraminated drinking water, thus all the methods were in agreement with this regard.

For total THM4, the concentrations ranged from 45.6 to 62.0 μg/L using USEPA 502.2 and 42.5 to 61.4 μg/L using CMS-GC. The average concentration was 53.3±3.8 μg/L using USEPA 502.2 and 55.1±4.7 μg/L for CMS-GC. Using CMS-GC, the bias ranged from −12.5 to 13.9 μg/L, with an average of 2.8±6.1 μg/L. In regards to the higher concentrations in the chloraminated water supply the two methods agree well. The CMS-GC inventive did not suffer major interferences in the chloraminated supply.

The preceding examples are set forth to illustrate the principles of the invention, and specific embodiments of operation of the invention. The examples are not intended to limit the scope of the method. Additional embodiments and advantages within the scope of the claimed invention will be apparent to one of ordinary skill in the art.

We claim:

1. A remote, on-line method of analyzing drinking water samples comprising the steps of:
    a) providing at least one stream of drinking water that has been disinfected with chlorinated or chloraminated materials;
    b) delivering said at least one stream of drinking water through a device that effectively and exclusively separates any volatile trihalomethane compounds from said at least one stream of drinking water into a stream of carrier gas and excludes any species that interferes with the measurement of such trihalomethane compounds therein; and
    c) delivering said stream of carrier gas including said volatile trihalomethane compounds through a multi-port valve for selective delivery to a chromatography analyzer, wherein said analyzer quantifies the amount of volatile trihalomethanes present within said carrier gas stream, which provides a reliable measurement of the total of such volatile trihalomethanes within said at least one stream of drinking water, wherein said multi-port valve alternates between delivering said carrier gas stream including said volatile trihalomethane compounds through to said chromatography analyzer or to a waste location by way of an actuator, wherein said method permits quantification of concentrations of individual trihalomethane compounds from the subject water sample as well as the concentration of the total amount of trihalomethane compounds within the same sample.

2. A drinking water analytical instrument comprising a capillary membrane sampling device for a drinking water stream trihalomethane separation process, wherein said capillary membrane sampling device allows for the exclusive separation of trihalomethane from said drinking water stream, and wherein said device is attached to a multi-port valve which selectively delivers either the separated trihalomethane stream or a purging gas stream to a chromatography analyzer, wherein said analyzer is utilized from a location remote from the user and provides analytical measurements for chlorinated or chloraminated water test samples in terms of amounts of total trihalomethane species as well as amounts of individual trihalomethane species.

* * * * *